United States Patent [19]
Schiller

[11] Patent Number: 6,150,335
[45] Date of Patent: Nov. 21, 2000

[54] TIC-CONTAINING OPIOID DIPEPTIDE DERIVATIVES USEFUL AS ANALGESICS

[75] Inventor: Peter Schiller, Montreal, Canada

[73] Assignee: Astra AB, Sweden

[21] Appl. No.: 09/043,881

[22] PCT Filed: Dec. 18, 1997

[86] PCT No.: PCT/SE97/02156

§ 371 Date: Apr. 1, 1998

§ 102(e) Date: Apr. 1, 1998

[87] PCT Pub. No.: WO98/28327

PCT Pub. Date: Jul. 2, 1998

[30] Foreign Application Priority Data

Dec. 20, 1996 [SE] Sweden .................................. 9604789

[51] Int. Cl.[7] .............................. A61K 38/05; C07K 5/065
[52] U.S. Cl. ............................................. 514/19; 546/146
[58] Field of Search ................................. 514/19; 546/146

[56] References Cited

FOREIGN PATENT DOCUMENTS

WO 96/06855  3/1996  WIPO .............................. C07K 5/065
WO 97/31940  9/1997  WIPO .............................. C07K 5/065

OTHER PUBLICATIONS

Title page for European Journal of Biochemistry, vol. 241, No. 3, Nov. 1996.
Calderon, et al., "Probes for Narcotic Receptor Mediated Phenomena 19. Synthesis of (+)-4[(αR)-α-((2S, 5R)-4-Allyl-2, 5-dimethyl-1-piperazinyl)-3-methoxybenzyl]-N,N-diethylbenzamide (SNC 80): A Highly Selective, Nonpeptide δ Opioid Receptor Agonist," *J. Med. Chem.* 37:2125–2128 (1994).
Carpenter, et al., "Role of Hydrophobic Substituents in the Interaction of Opioid Tyr–Tic Depeptide Analogs with Dodecylphosphocholine Micelles," *Eur. J. Biochem.* 241:756–764 (1996).
Chang, et al., "A Novel, Potent and Selective Nonpeptidic Delta Opioid Receptor Agonist BW373U86," *J. Pharmacol. Exper. Ther.* 267:852–857 (1993).
Cheng, et al., "Opioid–Induced Stimulation of Fetal Respiratory Activity by [D–Ala²]deltorphin I," *Eur. J. Pharmacol* 230:85–88 (1993).
Comer, et al., "Convulsive Effects of Systemic Administration of the Delta Opioid Agonist BW373U86 in Mice," *J. Pharmacol. Exper. Ther.* 267:888–895 (1993).
Cowan, et al., "Direct Dependence Studies in Rats with Agents Selective for Different Types of Opioid Receptor," *J. Pharmcacol. Exper. Ther.* 246:950–955 (1988).
Erspamer, et al., "Deltorphins: A Family of Naturally Occurring Peptides with High Affinity and Selectivity for δ Opioid Binding Sites," *Proc. Natl. Acad. Sci. USA* 86:5188–5192 (1989).
Gacel, et al. "Development of Conformationally Constrained Linear Peptides Exhibiting a High Affinity and Pronounced Selectivity for δ Opioid Receptors," *J. Med. Chem.* 31:1891–1897 (1988).

Galligan, et al., "Cerebral Delta Opioid Receptors Mediate Analgesia But Not the Intestinal Motility Effects of Intracerebroventricularly Administered Opioids," *J. Pharmacol Exper. Ther.* 229:641–648 (1984).
Kamei, et al., "Antinociceptive Effects of the Selective Non–Peptidic δ–Opioid Receptor Agonist TAN–67 in Diabetic Mice," *Eur. J. Pharmacol.* 276:131–135 (1995).
Mosberg, et al., "Bis–Penicillamine Enkephalins Possess Highly Improved Specificity Toward δ Opioid Receptors," *Proc. Natl. Acad. Sci. USA* 80:5871–5874 (1983).
Schiller, et al., "Differential Stereochemical Requirements of μ vs. δ Opioid Receptors for Ligand Binding and Signal Transduction: Development of a Class of Potent and Highly δ–Selective Peptide Antagonists," *Proc. Natl. Acad. Sci. USA* 89:11871–11875 (1992).
Schiller, et al., "Antagonism As a Consequence of Side Chain Conformational Restriction: A New Class of Potent, δ Opioid Receptor–Selective Peptide Antagonists," *Peptides 1992*:647–648 (1992).
Schiller, et al., "The TIPP Opioid Peptide Family: Development of a New Class of Highly Potent δ–Receptor Antagonists with Extraordinary δ–Selectivity," *Peptide Chemistry 1992*:337–340 (1992).
Schiller, et al., "A New Class of Potent and Highly Selective δ Opioid Receptor Peptide Antagonists Without μ Antagonist Properties," Abstr. 3699, *Faseb J.* 6:A1575 (1992).
Schiller, et al., "Novel Highly Selective δ Opioid Receptor Antagonists Without μ Antagonist Properties," *INRC Abstracts*:144 (1992).
Schiller, et al., "TIPP[ψ]: A Highly Potent and Stable Pseudopeptide δ Opioid Receptor Antagonist with Extraordinary δ Selectivity," *J. Med. Chem.* 36:3182–3187 (1993).
Schiller, et al., "TIPP Analogs: Highly Selective δ Opioid Antagonists with Subnanomolar Potency and First Known Compounds with Mixed μ Agonist/δ Antagonist Properties," *Proc. 24th INRC*:S63–S64 (1993).

(List continued on next page.)

*Primary Examiner*—Jeffrey E. Russel
*Attorney, Agent, or Firm*—Michael A. Sanzo; Pillsbury Madison & Sutro LLP

[57] ABSTRACT

Use of a compound of the formula I

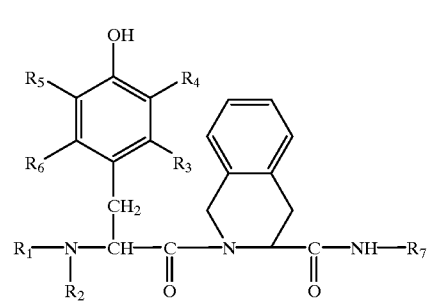

for the manufacture of a medicament for the treatment of pain. The compounds are δ opioid agonists and thus useful in the treatment of pain without the requirement of co-application of a μ opioid agonist.

4 Claims, No Drawings

OTHER PUBLICATIONS

Schiller, et al., "Novel Opioid Peptide Analogs with Mixed μ Agonist/δAntagonist Properties," *Peptides 1994*:632–633 (1994).

Schiller, et al., "Structure–Agonist/Antagonist Activity Relationships of TIPP Analogs," *Peptides: Chemistry, Structure and Biology*:609–611 (1995).

International Search Report for PCT/SE97/02156(Dated Mar. 30, 1999).

TIC-CONTAINING OPIOID DIPEPTIDE DERIVATIVES USEFUL AS ANALGESICS

FIELD OF THE INVENTION

This invention is related to a new use of opioid dipeptide derivatives with δ agonist properties, particularly as analgesic compounds.

BACKGROUND AND PRIOR ART

The results of recent studies indicated that opioid agonists that selectively act via δ receptors should have advantages over currently available opioid analgesics. In particular, potential advantages include the production of analgesia with i) decreased (or no) development of physical dependence (A. Cowan et al., J. Pharmacol. Exp. Ther. 246, 950–955 (1988));

ii) no depression (and the possible stimulation) of respiratory function (P. Y. Cheng et al., Eur. J. Pharmacol. 230, 85–88 (1993)); and iii) little or no adverse gastrointestinal effects (J. J. Galligan et al., J. Pharmacol. Exp. Ther. 229, 641–648 (1984).

Selective peptide δ agonists currently available include the enkephalin analogs H-Tyr-D-Thr-Gly-Phe-Leu-Thr-OH (DTLET; G. Gacel et al., J. Med. Chem. 31, 1891–1897 (1988)) and

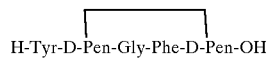

H-Tyr-D-Pen-Gly-Phe-D-Pen-OH (DPDPE, H. I. Mosberg et al., Proc Natl. Acad. Sci. USA 80, 5871–5874 (1983) and the deltorphins (H-Tyr-D-Met-Phe-His-Leu-Met-Asp-NH$_2$ (dermenkephalin)), H-Tyr-D-Ala-Phe-Asp-Val-Val-Gly-NH$_2$ (deltorphin I) and H-Tyr-D-Ala-Phe-Glu-Val-Val-Gly-NH$_2$ (deltorphin II); V. Erspamer et al., Proc. Natl. Acad. Sci. USA 86, 5188–5192 (1989)). However, these peptides are of relatively large molecular size (molecular weight>600) and for this reason their ability to cross the blood-brain barrier (BBB) is very limited.

Non-peptide δ agonists that have recently been developed include the racemic compound BW373U86 (K.-J. Chang et al., J. Pharmacol. Exp. Ther. 267, 852–857 (1993)) and its chemically modified enantiomer SNC80 (S.N. Calderon et al., J. Med. Chem. 37, 2125–2128 (1994)) as well as the compound TAN-67 (J. Kamei et al., Eur. J. Pharmacol. 276, 131–135 (1995)). However, BW 373U86 produced significant toxicity, manifested behaviorally as convulsions and barrel rolling, in mice (S. D. Comer et al., J. Pharmacol. Exp. Ther. 267, 888–895 (1993)), and TAN-67 showed no significant antinociceptive effect in the mouse tail flick test (J. Kamei et al., Eur. J. Pharmacol. 276, 131–135 (1995)). Therefore, there is still a need for the development of new potent δ opioid agonists of low molecular weight and high lipophilic character.

Peptides containing the N-terminal segment H-Tyr-Tic-Aaa (Tic=1,2,3,4-tetrahydroisoquinoline-3-carboxylic acid, Aaa=aromatic or aliphatic amino acid residue) that are very potent and highly selective δ opioid antagonists have recently been disclosed by P. W. Schiller et al., in FASEB J. 6(4), A1575 (1992), at the International Narcotics Research Conference (INRC) Meetings in Keystone, CO, Jun. 24–29 (1992) and in Skövde, Sweden, Jul. 10–15 (1993), at the 2nd Japan Symposium on Peptide Chemistry, Shizuoka, Japan, Nov. 9–13 (1992), at the 22nd European Peptide Symposium in Interlaken, Switzerland, Sept. 9–13 (1992), at the 14th American Peptide Symposium in Columbus, Ohio, Jun. 18–23 (1995), in Proc. Natl. Acad. Sci. USA 89, 11871–11875 (1992), and in J. Med. Chem. 36, 3182–3187 (1993).

Recently, it has been found that dipeptide derivatives of the type H-Tyr-Tic-NH—(CH$_2$)$_n$—Ph (Ph=phenyl) also have δ antagonist properties, if n=1, 3 or 4. In the case of n=2, however, the compound (H-Tyr-Tic-NH-CH$_2$—CH$_2$—Ph) surprisingly turned out to be a full, but only moderately potent δ agonist, as reported by P. W. Schiller et al. at the 23rd European Peptide Symposium in Braga, Portugal, Sept. 4–10, 1994.

Thus, the object of the present invention was to find structurally modified analogs of H-Tyr-Tic-NH—CH$_2$—CH$_2$—Ph with improved δ agonist potency. Compounds of this type should have potential for therapeutic use as centrally acting analgesics because their low molecular weight and lipophilic character can be expected to facilitate crossing of the BBB.

OUTLINE OF THE INVENTION

It has now been found that analogs of the dipeptide derivative H-Tyr-Tic-NH—CH$_2$—CH$_2$—Ph, as defined by the following formula I below, have high potency as δ opioid agonists and retain good δ receptor selectivity.

The present invention is directed to the use of compounds having the formula I

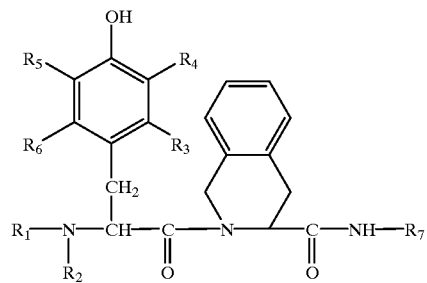

wherein

R$_1$ and R$_2$ is each and independently selected from H;

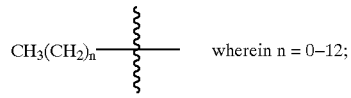    wherein n = 0–12;

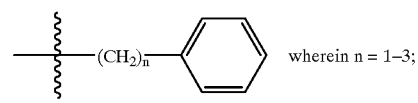    wherein n = 1–3;

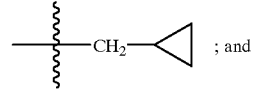    ; and

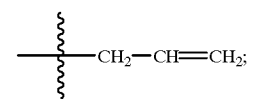

R$_3$, R$_4$, R$_5$, R$_6$ are all H; or

R$_4$, R$_5$, R$_6$ are all H, whereas R$_3$ is C$_1$–C$_6$ alkyl; or

R$_4$ and R$_5$ are both H, whereas R$_3$ and R$_6$ are both C$_1$–C$_6$ alkyl; or $R_3$, $R_5$, $R_6$ are all H, whereas $R_4$ is F, Cl, Br, I, OH, $NO_2$ or $NH_2$;

$R_7$ is a 2-phenylethyl- or a 2-cyclohexylethyl group containing one or more additional substituents in ortho- or para-position of the ring moiety or at the carbon atom adjacent to the ring moiety; for the manufacture of a medicament for use in the treatment of pain.

The compounds of the formula I above, are disclosed and claimed by the Applicant in the International patent application with the publication number WO 96/06855.

Illustrative examples of $R_7$ are:

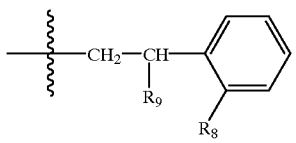
(i)

wherein $R_8$ is selected from H, F, Cl, Br, I, $NH_2$, $NO_2$, $C_1$–$C_6$ alkyl, and phenyl; and $R_9$ is selected from H, $C_1$–$C_6$ alkyl, —$CH_2OH$, and phenyl;

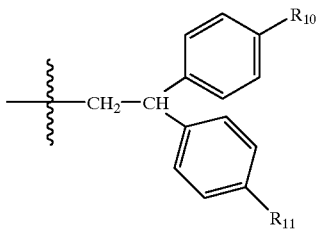
(ii)

wherein $R_{10}$ and $R_{11}$ is each and independently selected from H, $NO2$, $NH_2$, F, Cl, Br, I, and $C_1$–$C_6$ alkyl;

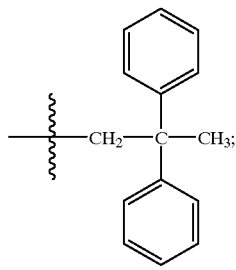
(iii)

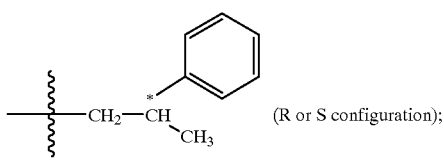
(iv)

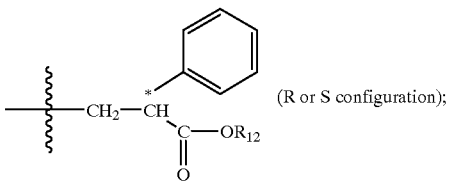
(v)

wherein $R_{12}$ is selected from anyone of $C_1$–$C_6$ alkyl and —$(CH_2)_n$—Ph, wherein n=0–3;

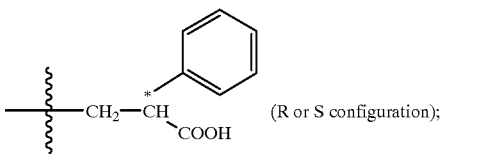
(vi)

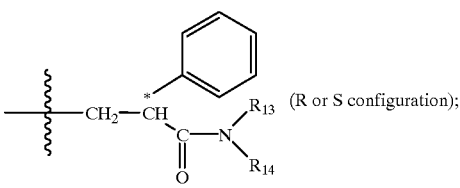
(vii)

wherein $R_{13}$ and $R_{14}$ is each and independently selected from anyone of H, $C_1$–$C_6$ alkyl, and —$(CH_2)_n$—Ph wherein n=0–3;

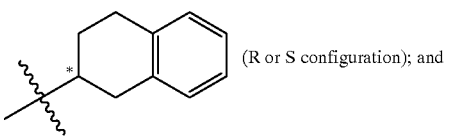
(viii)

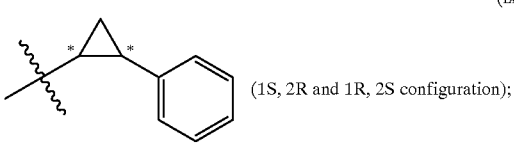
(ix)

Preferred compounds to use in accordance with the present invention are compounds wherein $R_1$ is selected from H and $CH_3$;

$R_2$ is selected from H and $CH_3$;

$R_3$ is selected from H and $CH_3$;

$R_4$ is H;

$R_5$ is H;

$R_6$ is selected from H and $CH_3$;
$R_7$ is selected from anyone of

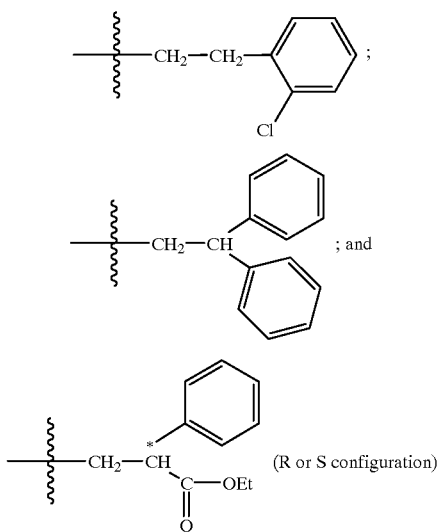

The compounds disclosed in accordance with the present invention are useful as analgesic agents. Thus, the compounds of the invention are useful in treating analgesia. The wording "analgesia" is defined as absence of pain in response to stimulation which would normally be painful. Since the compounds of the formula I above are δ agonists, they are effective in the treatment of pain without having to be administered in combination with a μ opioid agonist which is the case for compounds which are δ antagonists (E. E. Abdelhamid et al, *J. Pharmacol. Exp. Ther.* 258; pp. 299–303 (1991)).

Thus, one aspect of the present invention is the use of a compound of the formula I above for the manufacture of a medicament for use in the treatment of pain.

One further aspect of the present invention is a method for the treatment of pain, whereby is an effective amount of a compound according to formula I above, is administered to a subject suffering from pain.

Synthesis

Most Boc-amino acids used in the peptide syntheses are commercially available. 2-methyltyrosine (Mmt) was prepared by catalytic hydrogenation (Pd/C) of 7-hydroxy-1,2,3,4-tetrahydroisoquinoline-3-carboxylic acid (7-OH-Tic) in AcOH under $H_2$ pressure at 3 atm. 2',6'-dimethyltyrosine (Dmt) was prepared as described by J. H. Dygos et al. Synthesis, No. 8 (August) pp. 741–743 (1992). Most of the C-terminal amine substituents were also commercially available. 2-(2-bromophenyl)ethylamine, 2-(2-methylphenyl)ethylamine and 2,2-diphenylpropylamine were prepared by reduction of the corresponding nitriles with lithium aluminum hydride, as described by L. M. Amundsen and L. S. Nelson J. Am. Chem. Soc. 73, 242 (1951). 2-(2-biphenyl)ethylamine was synthesized as described by S. Goldschmidt and W. L. C. Veer Recueil 67, 489 (1948). Ethyl-α-phenyl-β-aminopropionate in racemic form was synthesized as described by E. Testa et al. Liebig's Ann. Chem. 614, 167 (1958). Acid hydrolysis of the latter product and subsequent amidation afforded racemic α-phenyl-β-aminopropionamide. 2,2-dicyclohexylethylamine was prepared from 2,2-diphenylethylamine by catalytic hydrogenation (Rh on carbon) at 6° C. under pressure (60 psi).

2,2-di-p-nitrophenylethylamine was prepared by nitration of 2,2-diphenylethylamine. 2,2-di-p-aminophenylethylamine was prepared by catalytic hydrogenation (Pd/C) of 2,2-di-p-nitrophenylethylamine. 2,2-di-p-chlorophenylethylamine was obtained from 2,2-di-p-aminophenylethylamine by diazotization of the aromatic amines followed by treatment with $Cu_2Cl_2$ (Sandmeyer reaction). α-Phenyl-β-aminopropanol was prepared by treatment of Boc-protected α-phenyl-β-aminopropionic acid with $BH_3$/TFA. 2-(2-nitrophenyl)ethylamine was obtained by reduction of 2-(2-nitrophenyl)ethylamine with $LiAlH_4$.

All dipeptide derivatives were prepared by solution synthesis by first coupling the C-terminal amine substituent to the carboxylic acid function of Boc-Tic-OH (mixed anhydride method), subsequent deprotection with acid, preferably an organic acid, especially preferred TFA, coupling of the Boc-protected N-terminal tyrosine or tyrosine analog (mixed anhydride method) and final deprotection with acid. The preferred acid system for Boc-deprotection is aqueous 95% TFA containing anisole (3%).

The HPLC system GOLD (Beckman) consisting of the programmable solvent module 126 and the diode array detector module 168 was used for the purification and the purity control of the peptides. Reversed-phase HPLC was performed using a gradient made from two solvents: (A) 0.1% TFA in water and (B) 0.1% TFA in acetonitrile. For preparative runs a Vidac 218TP1022 column (250×22 mm) was used with a linear gradient of 20–50% B over a period of 45 min at a flow rate of 13 ml/min, absorptions being measured at both 216 nm and 280 nm. The same gradient was used for analytical runs on a Vidac 218TP 0046 column (250×4.6 mm) over a period of 30 min at a flow rate of 1.0 ml/min. Purity of peptides was also established by TLC on precoated silica gel plates 60F-254 (E. Merck, Darmstadt, FRG) in the following solvent systems (all v/v): (A) $CHCl_3$/MeOH/AcOH (85:10:5) and (B) n-BuOH/$H_2$O/AcOH (4:1:1). Peptides were visualized with UV and with the ninhydrin spray reagent. Molecular weights of peptides were determined by FAB mass spectrometry on an MS-50 HMTCTA mass spectrometer interfaced with a DS-90 data system.

DETAILED DESCRIPTION OF THE INVENTION

The invention will now be described in more detail by the following examples.

Peptide Synthesis—General Methods

1) Mixed Anhydride Method

NMM (1 equiv.) was added to a stirred solution of 1 mmol of Boc-protected amino acid in THF. The mixture was cooled to −15° C., treated with IBCF (1 equiv.) and was allowed to react for 2 min. Subsequently, the amino component (1 equiv.) was added. The reaction mixture was stirred for 30 min at −15° C. and was then allowed to reach room temperature. The solvent was then removed by vacuum evaporation and the residual oil was dissolved in 100 ml of EtOAc. The resulting solution was extracted consecutively with 5% $KHSO_4$, brine and saturated $NaHCO_3$. The organic phase was dried ($MgSO_4$), filtered and evaporated to dryness. The resulting crude products were used for deprotection without prior purification.

2) Deprotection

The Boc-protected peptides were deprotected using aqueous 95% TFA containing thioanisole (3%) under stirring and cooling with ice. After evaporation in vacuo, the TFA salts of the peptides were obtained in pure form by preparative reversed-phase HPLC.

EXAMPLES

The invention will now be described by way of the following examples, where the compound of Example 1 in Table 1 has served as the illustrative example for the preparation of the compounds of the present invention. All the exemplified compounds have been prepared by following the same procedure as described for the compound of Example 1. These Examples should however not be construed as limiting the invention in any way.

Example 1

A) Preparation of H-Tic-NH—CH₂—CH—(Ph)₂ (Compound 1)

Boc-Tic-OH (0.4 mmol) was coupled with H₂N—CH₂—CH—(Ph)₂ (2,2-diphenylethylamine, 0.43 mmol) according to method 1. After deprotection compound 1 was obtained as a lyophilisate in 95% yield and was used as such in the next step of the synthesis without further purification.

TLC (silica): Rf=0.36 (A)

B) Preparation of H-Tyr-Tic-NH—CH₂—CH—(Ph)₂

Using the mixed anhydride method, Boc-Tyr(Boc)-OH (0.38 mmol) was coupled with the TFA salt of compound 1 (0.38 mmol) in the presence of NMM (2 equiv.). After deprotection the crude product was purified by HPLC. The compound in pure form was obtained in 85% yield.

FAB-MS: MH⁺=520

TLC (silica): Rf=0.75 (A), Rf=0.72 (B)

HPLC: K'=11.4

The compounds of Examples 2–31 have been synthesized as described for Example 1 above. In the case of the compounds of Examples 15 and 16, Examples 17 and 18, Examples 27 and 28 and Examples 30 and 31, the racemate of the C-terminal amine substituent was used in the synthesis and the resulting diastereomeric dipeptide derivatives were separated by preparative reversed-phase HPLC, using a Vidac 218TP0046 column (250×22 mm), under isocratic conditions: 43% MeOH-57% 0.1% TFA/H₂O (in the case of Examples 15 and 16, 17 and 18, and 30 and 31), or 34% MeOH-66% 0.1% TFA/H₂O (in the case of Examples 27 and 28).

In the case of compounds of Examples 21 and 22 the mixture of the two trans isomers of 2-phenylcyclopropylamine was used in the synthesis and the dipeptide isomers were separated by preparative reversed-phase HPLC, using a Vidac 218TP0046 column (250×22 mm) with the solvents (A) 0.1% TFA in water and (B) methanol under the following conditions: linear gradient of 20–55% B over a period of 25 min, followed by isocratic elution (45% A, 55% B) over a period of 30 min.

Examples of compounds prepared for use according to the invention are given below in Table 1.

TABLE 1

| EXAMPLE | COMPOUND | Molecular Weight (FAB-MS) [MH⁺] |
|---|---|---|
| 1 | H-Tyr-Tic-NH—CH₂—CH(Ph)₂ | 520 |
| 2 | H-D-Dmt-Tic-NH—(CH₂)₂—Ph | 472 |
| 3 | H-Tyr-Tic-NH—(CH₂)₂—(2-F-C₆H₄) | 462 |
| 4 | H-Tyr-Tic-NH—(CH₂)₂—(2-Cl-C₆H₄) | 478 |
| 5 | H-Tyr-Tic-NH—(CH₂)₂—(2-Br-C₆H₄) | 523 |
| 6 | H-Tyr-Tic-NH—(CH₂)₂—(2-CH₃-C₆H₄) | 458 |
| 7 | H-Tyr-Tic-NH—(CH₂)₂—(2-Ph-C₆H₄) | 520 |
| 8 | H-Dmt-Tic-NH—(CH₂)₂—Ph | 472 |
| 9 | Tyr(NMe)-Tic-NH—CH₂—CH(Ph)₂ | 534 |

TABLE 1-continued

| EXAMPLE | COMPOUND | Molecular Weight (FAB-MS) [MH+] |
|---|---|---|
| 10 | H-Dmt-Tic-NH—CH$_2$—CH(C$_6$H$_5$)$_2$ | 548 |
| 11 | H-D-Dmt-Tic-NH—CH$_2$—CH(C$_6$H$_5$)$_2$ | 548 |
| 12 | H-Tyr-Tic-NH—CH$_2$—C(CH$_3$)(C$_6$H$_5$)$_2$ | 534 |
| 13 | H-Tyr-Tic-NH—CH$_2$—CH(CH$_3$)(C$_6$H$_5$) (S) | 458 |
| 14 | H-Tyr-Tic-NH—CH$_2$—CH(CH$_3$)(C$_6$H$_5$) (R) | 458 |
| 15 | H-Tyr-Tic-NH—CH$_2$—*CH(C$_6$H$_5$)(COOEt) (Diastereomer I) | 516 |
| 16 | H-Tyr-Tic-NH—CH$_2$—*CH(C$_6$H$_5$)(COOEt) (Diastereomer II) | 516 |
| 17 | H-Tyr-Tic-NH—CH$_2$—*CH(C$_6$H$_5$)(CONH$_2$) (Diastereomer I) | 487 |
| 18 | H-Tyr-Tic-NH—CH$_2$—*CH(C$_6$H$_5$)(CONH$_2$) (Diastereomer II) | 487 |
| 19 | H-Tyr-Tic-2-S-At (At = aminotetralin) | 470 |
| 20 | H-Tyr-Tic-2-R-At (At = aminotetralin) | 470 |
| 21 | H-Tyr-Tic-NH—(cyclopropyl-C$_6$H$_5$) (Trans isomer I) | 456 |
| 22 | H-Tyr-Tic-NH—(cyclopropyl-C$_6$H$_5$) (Trans isomer II) | 456 |
| 23 | H-Tyr-Tic-NH—CH$_2$—CH(cyclohexyl)$_2$ | 532 |
| 24 | H-Tyr-Tic-NH—CH$_2$—CH(4-NO$_2$-C$_6$H$_4$)$_2$ | 610 |

TABLE 1-continued

| EX-AMPLE | COMPOUND | Molecular Weight (FAB-MS) [MH+] |
|---|---|---|
| 25 | H-Tyr-Tic-NH—CH$_2$—CH(C$_6$H$_4$-NH$_2$)$_2$ | 550 |
| 26 | H-Tyr-Tic-NH—CH$_2$—CH(C$_6$H$_4$-Cl)$_2$ | 589 |
| 27 | H-Tyr-Tic-NH—CH$_2$—*CH(Ph)(CH$_2$OH) (I) | 474 |
| 28 | H-Tyr-Tic-NH—CH$_2$—*CH(Ph)(CH$_2$OH) (II) | 474 |
| 29 | H-Tyr-Tic-NH—(CH$_2$)$_2$—(2-NO$_2$-C$_6$H$_4$) | 489 |
| 30 | H-Mmt-Tic-NH—CH$_2$—CH(Ph)(COOEt) (I) | 530 |
| 31 | H-Mmt-Tic-NH—CH$_2$—CH(Ph)(COOEt) (II) | 530 |

Pharmacological Testing in vitro of δ Opioid Agonists

Bioassays based on inhibition of electrically evoked contractions of the mouse vas deferens (MVD) and of the guinea pig ileum (GPI) were performed. In the GPI assay the opioid effect is primarily mediated by μ opioid receptors, whereas in the MVD assay the inhibition of the contractions is mostly due to interaction with δ opioid receptors. Agonist potencies are expressed as IC50 values (concentration of the agonist that produces 50% inhibition of the electrically induced contractions).

Bioassays Using Isolated Organ Preparations

The GPI and MVD bioassays were carried out as reported in P. W. Schiller et al., Biochem. Biophys. Res. Commun. 85, 1332–1338 (1978) and J. DiMaio et al., J. Med. Chem. 25, 1432–1438 (1982). A log-dose response curve was determined with [Leu$^5$]enkephalin as standard for each ileum and vas preparation, and IC50 values of the compounds being tested were normalized according to A. A. Waterfield et al., Eur. J. Pharmacol. 58, 11–18 (1979). The results are shown in Table 2 below.

TABLE 2

Guinea pig ileum (GPI) and mouse vas deferens (MVD) assay of dipeptide derivatives with δ opioid agonist properties.

| EX. NO. | COMPOUND | GPI IC$_{50}$ [nM] | MVD IC$_{50}$ [nM] | GPI/MVD IC$_{50}$ ratio |
|---|---|---|---|---|
| | H-Tyr-Tic-NH—(CH$_2$)$_2$—Ph | 2120 ± 640 | 82.0 ± 10.0 | 25.9 |

TABLE 2-continued

Guinea pig ileum (GPI) and mouse vas deferens (MVD) assay of dipeptide derivatives with δ opioid agonist properties.

| EX. NO. | COMPOUND | GPI IC$_{50}$ [nM] | MVD IC$_{50}$ [nM] | GPI/MVD IC$_{50}$ ratio |
|---|---|---|---|---|
| 1 | 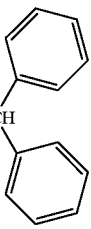 H-Tyr-Tic-NH—CH$_2$—CH(C$_6$H$_5$)$_2$ | 3630 ± 470 | 3.77 ± 1.05 | 963 |
| 2 |  H-D-Dmt-Tic-NH—(CH$_2$)$_2$—C$_6$H$_5$ | 290 ± 4 | 10.4 ± 1.4 | 27.9 |
| 3 | 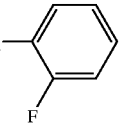 H-Tyr-Tic-NH—(CH$_2$)$_2$—C$_6$H$_4$-F | 5450 ± 1800 | 75.5 ± 8.5 | 72.2 |
| 4 | 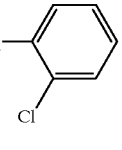 H-Tyr-Tic-NH—(CH$_2$)$_2$—C$_6$H$_4$-Cl | partial agonist | 8.77 ± 1.28 | — |
| 5 | 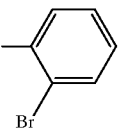 H-Tyr-Tic-NH—(CH$_2$)$_2$—C$_6$H$_4$-Br | 613 ± 26 | 13.9 ± 1.9 | 44.1 |
| 6 | 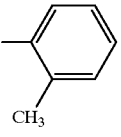 H-Tyr-Tic-NH—(CH$_2$)$_2$—C$_6$H$_4$-CH$_3$ | 759 ± 152 | 10.1 ± 1.2 | 75.1 |
| 7 | 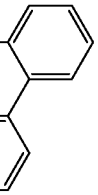 H-Tyr-Tic-NH—(CH$_2$)$_2$—C$_6$H$_4$-C$_6$H$_5$ | >10 000 | 418 ± 55 | >23.9 |
| 8 |  H-Dmt-Tic-NH—(CH$_2$)$_2$—C$_6$H$_5$ | 48.0 ± 3.6 | 2.30 ± 0.61 (partial agonist; max inhib. = 74%) | 20.9 |

TABLE 2-continued

Guinea pig ileum (GPI) and mouse vas deferens (MVD) assay of dipeptide derivatives with δ opioid agonist properties.

| EX. NO. | COMPOUND | GPI IC$_{50}$ [nM] | MVD IC$_{50}$ [nM] | GPI/MVD IC$_{50}$ ratio |
|---|---|---|---|---|
| 9 | Tyr(NMe)-Tic-NH—CH$_2$—CH(C$_6$H$_5$)$_2$ 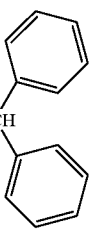 | 156 ± 62 | 0.261 ± 0.046 | 598 |
| 10 | H-Dmt-Tic-NH—CH$_2$—CH(C$_6$H$_5$)$_2$ 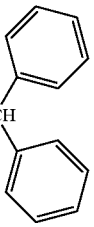 | 290 ± 38 | 0.726 ± 0.273 | 399 |
| 11 | H-D-Dmt-Tic-NH—CH$_2$—CH(C$_6$H$_5$)$_2$ 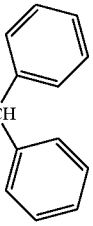 | 91.1 ± 33.4 | 3.01 ± 1.04 | 30.3 |
| 12 | H-Tyr-Tic-NH—CH$_2$—C(C$_6$H$_5$)$_2$—CH$_3$ 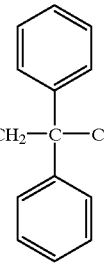 | 2830 ± 990 | 93.4 ± 18.4 | 30.3 |
| 13 | H-Tyr-Tic-NH—CH$_2$—CH(C$_6$H$_5$)(CH$_3$) (S) 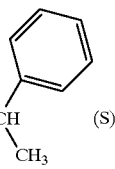 | 3790 ± 640 | 21.4 ± 8.2 | 177 |
| 14 | H-Tyr-Tic-NH—CH$_2$—CH(CH$_3$)(C$_6$H$_5$) (R) 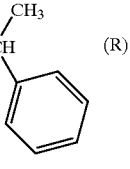 | 3430 ± 490 | 26.0 ± 2.5 | 132 |

TABLE 2-continued

Guinea pig ileum (GPI) and mouse vas deferens (MVD) assay of dipeptide derivatives with δ opioid agonist properties.

| EX. NO. | COMPOUND | GPI IC$_{50}$ [nM] | MVD IC$_{50}$ [nM] | GPI/MVD IC$_{50}$ ratio |
|---|---|---|---|---|
| 15 | H-Tyr-Tic-NH—CH$_2$—*CH(Ph)COOEt (Diastereomer I) | >10 000 | 1.28 ± 0.18 | 7810 |
| 16 | H-Tyr-Tic-NH—CH$_2$—*CH(Ph)COOEt (Diastereomer II) | >10 000 | 8.64 ± 1.31 | 1160 |
| 17 | H-Tyr-Tic-NH—CH$_2$—*CH(Ph)CONH$_2$ (Diastereomer I) | 2140 ± 470 | 34.0 ± 2.9 | 62.9 |
| 18 | H-Tyr-Tic-NH—CH$_2$—*CH(Ph)CONH$_2$ (Diastereomer II) | >10 000 | partial agonist | — |
| 19 | H-Tyr-Tic-2-S-At (At = aminotetralin) | 1710 ± 230 | 38.1 ± 12.2 | 44.9 |
| 20 | H-Tyr-Tic-2-R-At (At = aminotetralin) | partial agonist | 36.3 ± 3.58 | — |
| 21 | H-Tyr-Tic-NH-cyclopropyl-Ph (Trans isomer I) | 1600 ± 500 | partial agonist | — |
| 22 | H-Tyr-Tic-NH-cyclopropyl-Ph (Trans isomer II) | 518 ± 147 | 7.31 ± 2.30 | 70.9 |
| 23 | H-Tyr-Tic-NH—CH$_2$—CH(cyclohexyl)$_2$ | 1580 ± 610 | 21.5 ± 6.8 | 73.5 |

TABLE 2-continued

Guinea pig ileum (GPI) and mouse vas deferens (MVD) assay of dipeptide derivatives with δ opioid agonist properties.

| EX. NO. | COMPOUND | GPI IC$_{50}$ [nM] | MVD IC$_{50}$ [nM] | GPI/MVD IC$_{50}$ ratio |
|---|---|---|---|---|
| 24 | 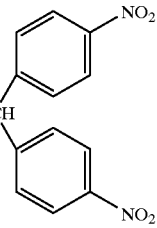 H-Tyr-Tic-NH—CH$_2$—CH(4-NO$_2$-C$_6$H$_4$)$_2$ | 5200 ± 1100 | 8.91 ± 1.53 | 584 |
| 25 | 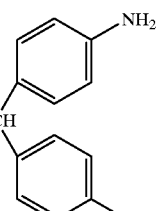 H-Tyr-Tic-NH—CH$_2$—CH(4-NH$_2$-C$_6$H$_4$)$_2$ | >10 000 | 7.81 ± 0.48 | >1280 |
| 26 | 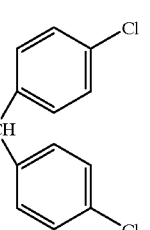 H-Tyr-Tic-NH—CH$_2$—CH(4-Cl-C$_6$H$_4$)$_2$ | >10 000 | 397 ± 33 | >25.2 |
| 27 | 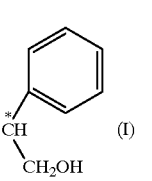 H-Tyr-Tic-NH—CH$_2$—CH(Ph)(CH$_2$OH) (I) | 526 ± 51 | 13.6 ± 2.2 | 38.7 |
| 28 | 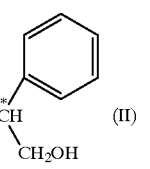 H-Tyr-Tic-NH—CH$_2$—CH(Ph)(CH$_2$OH) (II) | >10 000 | 92.6 ± 6.0 | >108 |
| 29 | 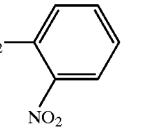 H-Tyr-Tic-NH—(CH$_2$)$_2$—(2-NO$_2$-C$_6$H$_4$) | 1850 ± 540 | 29.1 ± 10.6 | 63.6 |
| 30 | 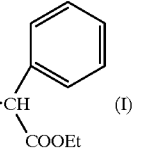 H-Mmt-Tic-NH—CH$_2$—CH(Ph)(COOEt) (I) | 826 ± 183 | 1.62 ± 0.12 | 510 |

TABLE 2-continued

Guinea pig ileum (GPI) and mouse vas deferens (MVD) assay of dipeptide derivatives with δ opioid agonist properties.

| EX. NO. | COMPOUND | GPI IC$_{50}$ [nM] | MVD IC$_{50}$ [nM] | GPI/MVD IC$_{50}$ ratio |
|---|---|---|---|---|
| 31 | 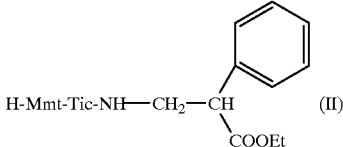 | 869 ± 209 | 2.24 ± 0.33 | 388 |

Conclusion

Based on the results from the performed MVD and GPI assays, the following conclusions could be made:

All compounds were full δ opioid agonists, with the exception of the compounds of Examples 8, 18, and 21, which have shown to be partial δ agonists.

All compounds showed weak μ agonist or partial μ agonist properties

Opioid Receptor Binding Assays

μ and δ opioid receptor binding constants ($K_i^\mu$, $K_i^\delta$) of the compounds were determrined by displacement of relatively selective μ and δ radioligands from binding sites in rat brain membrane preparations calculated from the measured IC50 values on the basis of the equation by Cheng and Prusoff, (Y. C. Cheng and W. H. Prusoff Biochem. Pharmnacol. 22, 3099–3102 (1973)).

The ratio $K_i^\mu/K_i^\delta$ was a quantitative measure of the δ versus μ receptor selectivity.

Opioid Receptor Binding Studies

The μ-, δ- and κ-opioid receptor affinities of all new analogs were determined in binding assays based on displacement of μ-, δ- and κ-selective radioligands from rat brain membrane binding sites. In the case of κ-ligands guinea pig brain homogenates were used, since the relative proportion of κ-binding sites is higher in guinea pig brain than in rat brain. The experimental procedure being used in our laboratory represents a modified version of the binding assay described by Pasternak et al. (Mol. Pharnacol. 11, 340–351 (1975)). Male Sprague-Dawley rats (300–350 g) from the Canadian Breeding Laboratories were decapitated and after removal of the cerebellum the brains were homogenized in 30 volumes of ice-cold standard buffer (50 mnM Tris HCl, pH 7.7). After centrifugation at 30,000×g for 30 min at 4° C. the membranes were reconstituted in the original volume of standard buffer and incubated for 30 min at 37° C. (to release bound endogenous ligands). Subsequent centrifugation and resuspension of the pellet in the initial volume of fresh standard buffer yielded the final membrane suspension. Aliquots (2 ml) of the membrane preparations were incubated for 1–2 h at 25° C. with 1 ml standard buffer containing the peptide to be tested and one of the following radioligands at the final concentration indicated: [$^3$H] DAMGO, μ-selective, 0.7 nM; [$^3$H]DSLET, μ-selective, 1.0 nM; and [$^3$H]U69,563, κ-selective, 0.5 nM. The incubation was terminated by filtration through Whatman GF/B filters under vacuum at 4° C. Following two washings with 5 ml portions of ice-cold standard buffer the filters were transferred to scintillation vials and treated with 1 ml Protosol (New England Nuclear) for 30 min prior to addition of 0.5 ml acetic acid and 10 ml Aquasol (New England Nuclear). After shaking for 30 min the vials were counted at an efficiency of 40–45%. All experiments were performed in duplicate and repeated at least three times. Specific binding of each of the three radioligands was defined by performing incubations in the presence of cold DAMGO, DSLET and U69,563, respectively, at a concentration of 1 micromolar. Values of half-maximal inhibition (IC50) of specific binding were obtained graphically from semilogarithmic plots. From the measured IC50-values, binding inhibition constants ($K_i$) were calculated based on Cheng and Prusoff's equation (Biochem. Pharmacol. 22, 3099–3102 (1973)). Ratios of the $K_i$-values determined in the μ-, δ- and κ-representative binding assays are a measure of the receptor selectivity of the compound under investigation (e.g. $K_i^\mu/K_i^\mu$ indicates the selectivity for δ-receptors versus μ-receptors). The results are shown in Table 3 below.

TABLE 3

Opioid receptor binding assays of dipeptide derivatives with δ opioid receptor agonist properties

| EX.NO. | COMPOUND | $K_i^\mu$ [nM] | $K_i^\delta$ [nM] | $K_i^\mu/K_i^\delta$ |
|---|---|---|---|---|
| | 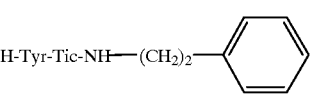 | 69.1 ± 1.9 | 5.22 ± 0.02 | 13.2 |

TABLE 3-continued

Opioid receptor binding assays of dipeptide derivatives with δ opioid receptor agonist properties

| EX.NO. | COMPOUND | $K_i^\mu$ [nM] | $K_i^\delta$ [nM] | $K_i^\mu/K_i^\delta$ |
|---|---|---|---|---|
| 1 | H-Tyr-Tic-NH—CH₂—CH(C₆H₅)₂ | 28.8 ± 4.2 | 0.981 ± 0.038 | 29.4 |
| 2 | H-D-Dmt-Tic-NH—(CH₂)₂—C₆H₅ | 8.20 ± 0.19 | 4.51 ± 0.66 | 1.82 |
| 3 | H-Tyr-Tic-NH—(CH₂)₂—(2-F-C₆H₄) | 255 ± 3 | 7.71 ± 1.17 | 33.1 |
| 4 | H-Tyr-Tic-NH—(CH₂)₂—(2-Cl-C₆H₄) | 96.9 ± 9.6 | 1.43 ± 0.09 | 67.8 |
| 5 | H-Tyr-Tic-NH—(CH₂)₂—(2-Br-C₆H₄) | 23.3 ± 7.7 | 1.24 ± 0.27 | 18.8 |
| 6 | H-Tyr-Tic-NH—(CH₂)₂—(2-CH₃-C₆H₄) | 38.7 ± 8.9 | 1.75 ± 0.10 | 22.1 |
| 7 | H-Tyr-Tic-NH—(CH₂)₂—(2-biphenyl) | 73.5 ± 7.1 | 4.76 ± 1.70 | 15.4 |
| 8 | H-Dmt-Tic-NH—(CH₂)₂—C₆H₅ | 1.59 ± 0.14 | 0.0577 ± 0.0049 | 27.6 |
| 9 | Tyr(NMe)-Tic-NH—CH₂—CH(C₆H₅)₂ | 12.7 ± 1.2 | 0.581 ± 0.096 | 21.9 |

TABLE 3-continued

Opioid receptor binding assays of dipeptide derivatives
with δ opioid receptor agonist properties

| EX.NO. | COMPOUND | $K_i^\mu$ [nM] | $K_i^\delta$ [nM] | $K_i^\mu/K_i^\delta$ |
|---|---|---|---|---|
| 10 | 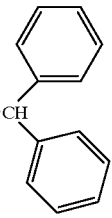 H-Dmt-Tic-NH—CH$_2$—CH(Ph)(Ph) | 1.62 ± 0.12 | 0.693 ± 0.126 | 2.34 |
| 11 | 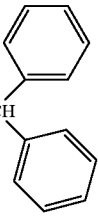 H-D-Dmt-Tic-NH—CH$_2$—CH(Ph)(Ph) | 4.08 ± 0.19 | 1.75 ± 0.10 | 2.33 |
| 12 | 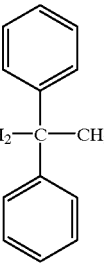 H-Tyr-Tic-NH—CH$_2$—C(Ph)(Ph)—CH$_3$ | 22.9 ± 0.05 | 20.0 ± 4.0 | 1.15 |
| 13 | 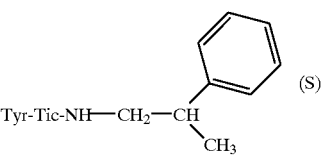 H-Tyr-Tic-NH—CH$_2$—CH(Ph)(CH$_3$) (S) | 82.3 ± 17.7 | 6.31 | 13.0 |
| 14 | 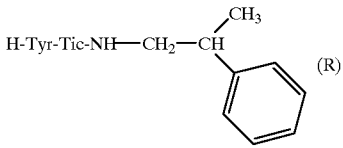 H-Tyr-Tic-NH—CH$_2$—CH(CH$_3$)(Ph) (R) | 51.3 | 3.67 | 14.0 |
| 15 | 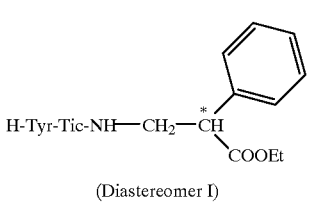 H-Tyr-Tic-NH—CH$_2$—CH*(Ph)(COOEt) (Diastereomer I) | 886 ± 172 | 0.569 ± 0.080 | 1560 |

TABLE 3-continued

Opioid receptor binding assays of dipeptide derivatives
with δ opioid receptor agonist properties

| EX.NO. | COMPOUND | $K_i^\mu$ [nM] | $K_i^\delta$ [nM] | $K_i^\mu/K_i^\delta$ |
|---|---|---|---|---|
| 16 | H-Tyr-Tic-NH—CH$_2$—*CH(Ph)(COOEt) (Diastereomer II) | 153 ± 5 | 3.03 ± 0.66 | 50.5 |
| 17 | H-Tyr-Tic-NH—CH$_2$—CH(Ph)(CONH$_2$) (Diastereomer I) | 73.7 ± 0.6 | 21.5 ± 4.2 | 3.43 |
| 18 | H-Tyr-Tic-NH—CH$_2$—*CH(Ph)(CONH$_2$) (Diastereomer II) | 191 ± 19 | 22.8 ± 2.5 | 8.38 |
| 19 | H-Tyr-Tic-2-S-At (At = aminotetralin) | 55.8 ± 6.3 | 4.55 ± 1.03 | 12.3 |
| 20 | H-Tyr-Tic-2-R-At (At = aminotetralin) | 26.3 ± 2.3 | 1.72 ± 0.17 | 15.3 |
| 21 | H-Tyr-Tic-NH-cyclopropyl-Ph (Trans isomer I) | 38.0 ± 11.2 | 4.13 ± 0.27 | 9.20 |
| 22 | H-Tyr-Tic-NH-cyclopropyl-Ph (Trans isomer II) | 11.5 ± 1.1 | 1.36 ± 0.15 | 8.46 |
| 23 | H-Tyr-Tic-NH—CH$_2$—CH(cyclohexyl)$_2$ | 52.4 ± 2.5 | 11.3 ± 3.3 | 4.64 |

TABLE 3-continued

Opioid receptor binding assays of dipeptide derivatives with δ opioid receptor agonist properties

| EX.NO. | COMPOUND | $K_i^\mu$ [nM] | $K_i^\delta$ [nM] | $K_i^\mu/K_i^\delta$ |
|---|---|---|---|---|
| 24 | H-Tyr-Tic-NH—CH$_2$—CH(4-NO$_2$-C$_6$H$_4$)$_2$ | 635 ± 109 | 7.17 ± 0.24 | 88.6 |
| 25 | H-Tyr-Tic-NH—CH$_2$—CH(4-NH$_2$-C$_6$H$_4$)$_2$ | 5340 ± 700 | 2.67 ± 0.83 | 2000 |
| 26 | H-Tyr-Tic-NH—CH$_2$—CH(4-Cl-C$_6$H$_4$)$_2$ | 1560 ± 60 | 2.82 ± 0.07 | 553 |
| 27 | H-Tyr-Tic-NH—CH$_2$—CH*(C$_6$H$_5$)(CH$_2$OH) (I) | 70.3 ± 2.3 | 1.26 ± 0.11 | 55.8 |
| 28 | H-Tyr-Tic-NH—CH$_2$—CH*(C$_6$H$_5$)(CH$_2$OH) (II) | 242 ± 20 | 7.80 ± 2.80 | 31.0 |
| 29 | H-Tyr-Tic-NH—(CH$_2$)$_2$-(2-NO$_2$-C$_6$H$_4$) | 355 ± 13 | 7.70 ± 0.45 | 46.1 |
| 30 | H-Mmt-Tic-NH—CH$_2$—CH(C$_6$H$_5$)(COOEt) (I) | 164 ± 11 | 1.63 ± 0.27 | 101 |

TABLE 3-continued

Opioid receptor binding assays of dipeptide derivatives with δ opioid receptor agonist properties

| EX.NO. | COMPOUND | $K_i^\mu$ [nM] | $K_i^\delta$ [nM] | $K_i^\mu/K_i^\delta$ |
|---|---|---|---|---|
| 31 | H-Mmt-Tic-NH—CH$_2$—CH(COOEt)—C$_6$H$_5$ (II) | 79.7 ± 2.3 | 1.22 ± 0.04 | 65.3 |

Conclusion

Based on the results of the performed opioid receptor binding assays, the following conclusions could be made:
  All compounds showed high δ opioid receptor affinity
  All compounds showed preference for δ receptors over μ receptors
  None of the compounds had significant affinity for κ receptors Potential Use The described compounds represent a novel class of δ agonists. δ Agonists are of interest as therapeutic agents for use in analgesia because, unlike the traditionally used μ agonists (e.g. morphine), they produce less or no physical dependence, no respiratory depression and less or no adverse gastrointestinal effects. In comparison with the well-known larger δ opioid peptide agonists (DPDPE, deltorphin, etc.), the compounds according to the claimed invention have a much lower molecular weight and higher lipophilic character. Therefore, these compounds can be expected to cross the BBB after peripheral administration and to produce a centrally mediated analgesic effect.

Abbreviations

BBB=blood-brain barrier
Boc=tert-butoxycarbonyl
BW373U86=(±)-4-(a-R*)-a-(2S*,5R*)-4-allyl-2,5-dimethyl-1-piperazinyl)-3-hydroxybenzyl)-N,N-diethylbenzamide
DAMGO=H-Tyr-D-Ala-Gly-Phe(N$_{Me}$)-Gly-ol
Dmt=2',6'-dimethyltyrosine DPDPE = [D-Pen$^2$,D-Pen$^5$]enkephalin DSLET=H-Tyr-D-Ser-Gly-Phe-Leu-Thr-OH
DTLET=H-Tyr-D-Thr-Gly-Phe-Leu-Thr-OH
FAB-MS=fast atom bombardment mass spectrometry
GPI=guinea pig ileum
HPLC=high performance liquid chromatography
IBCF=isobutylchloroformate
MVD=mouse vas deferens
NMM=N-methylmorpholine
Ph=phenyl
SNC80=(+)-4-(a-R*)-a-(2S*,5R*)-4-allyl-2,5-dimethyl-1-piperazinyl)-3-methoxybenzyl)-N,N-diethylbenzamide
TAN-67=2-methyl-4α,α-(3-hydroxyphenyl)-1,2,3,4,4a,5,12,12aα-octahydroquinolino[2,3,3-g]isoquinoline
TFA=trifluoroacetic acid
THF=tetrahydrofuran
Tic=1,2,3,4-tetrahydroisoquinoline-3-carboxylic acid
TLC=thin layer chromatography
U69,593=(5α,7α,8β)-(—)-N-methyl-[7-(pyrrolidinyl)-1-oxaspiro[4,5]dec-8-yl]benzeneacetamide

What is claimed is:

1. A method of treating a patient for pain comprising, administering to said patient an effective amount of a compound of formula I:

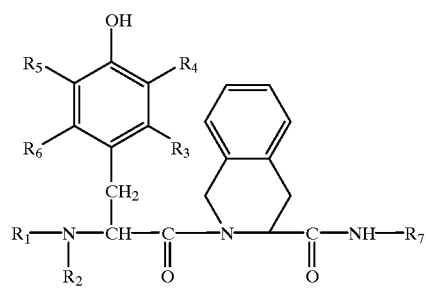

wherein
  $R_1$ and $R_2$ is each and independently selected from H;

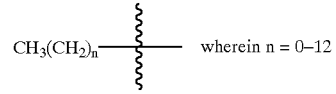  wherein n = 0–12

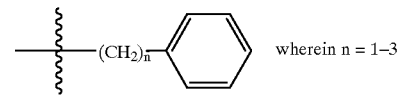  wherein n = 1–3

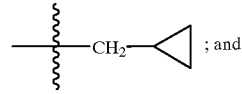 ; and

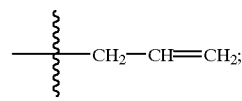

$R_3$, $R_4$, $R_5$, $R_6$ are all H; or
  $R_4$, $R_5$, $R_6$ are all H whereas $R_3$ is a $C_1$–$C_6$ alkyl; or
  $R_4$ and $R_5$ are both H, whereas $R_3$ and $R_6$ are both a $C_1$–$C_6$ alkyl; or
  $R_3$, $R_5$, $R_6$ are all H, whereas $R_4$ is F, Cl, Br, I, OH, $NO_2$ or $NH_2$;
  $R_7$ is a 2-phenylethyl- or a 2-cyclohexylethyl group containing one or more additional substituents in the ortho- or para-position of the ring moiety or at the carbon atom adjacent to the ring moiety, with the proviso that, when $R_1$ and $R_2$ are both H, $R_7$ is not a 2-phenylethyl group substituted in the para position.

2. A method of treating a patient for pain, comprising administering to said patient an effective amount of a compound of formula I:

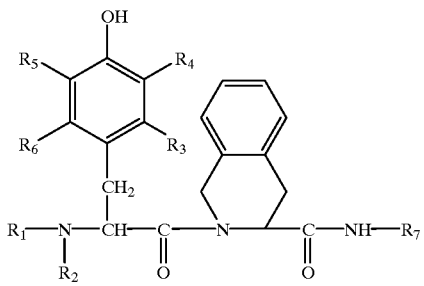

wherein:

$R_1$ is selected from H and $CH_3$;
$R_2$ is selected from H and $CH_3$;
$R_3$ is selected from H and $CH_3$;
$R_4$ is H;
$R_5$ is H;
$R_6$ is selected from H and $CH_3$;
$R_7$ is selected from any one of

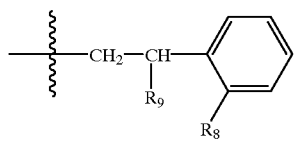 (i)

wherein $R_8$ is selected from H, F, Cl, Br, I, $NH_2$, $NO_2$, $C_1$–$C_6$ alkyl, and phenyl; and $R_9$ is selected from H, $C_1$–$C_6$ alkyl, —$CH_2OH$, and phenyl;

with the proviso that $R_8$ and $R_9$ may not both be H;

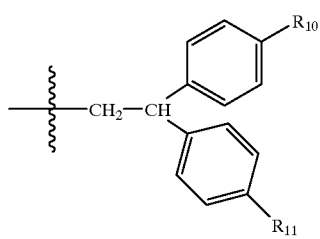 (ii)

wherein $R_{10}$ and $R_{11}$ is each and independently selected from H, $NO_2$, $NH_2$, F, Cl, Br, I, and $C_1$–$C_6$ alkyl;

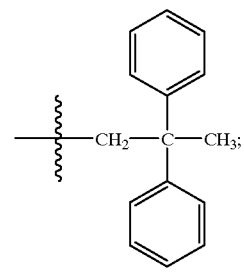 (iii)

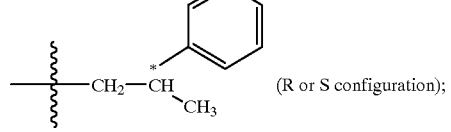 (iv)

(R or S configuration);

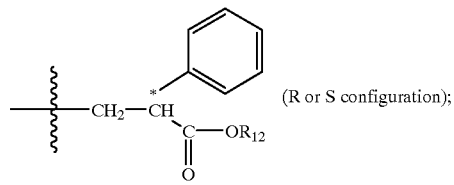 (v)

(R or S configuration);

wherein $R_{12}$ is selected from $C_1$–$C_6$ alkyl and (—$CH_2$)$_n$—Ph, wherein n=0–3;

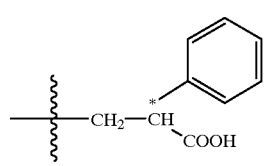 (vi)

(R or S configuration);

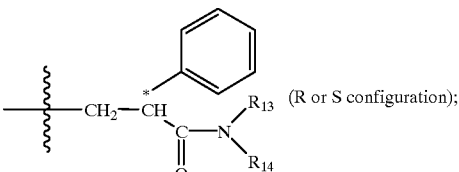 (vii)

(R or S configuration);

wherein $R_{13}$ and $R_{14}$ is each and independently selected from H, $C_1$–$C_6$ alkyl, and —($CH_2$)$_n$—Ph wherein n=0–3;

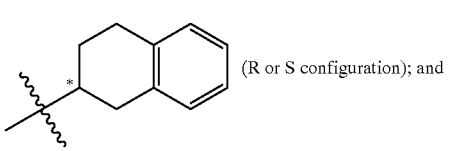 (viii)

(R or S configuration); and (ix)
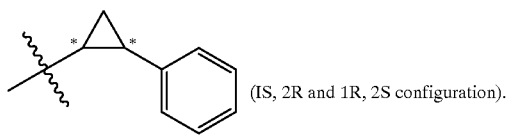
(1S, 2R and 1R, 2S configuration).
3. A method of treating a patient for pain, comprising administering to said patient an effective amount of a compound selected from the group consisting of:
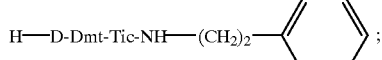
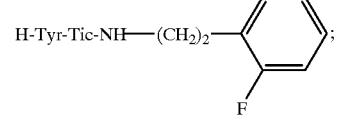
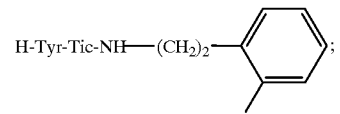
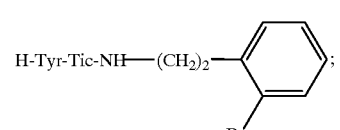
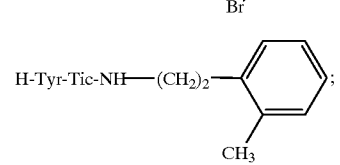
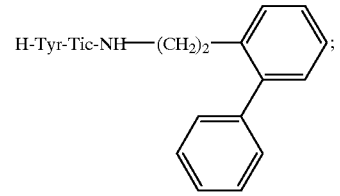
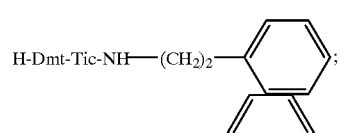
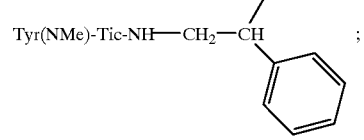
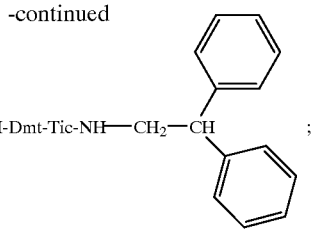
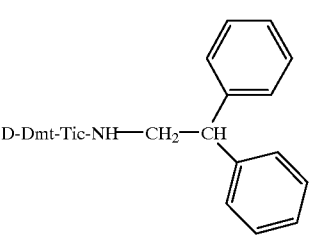
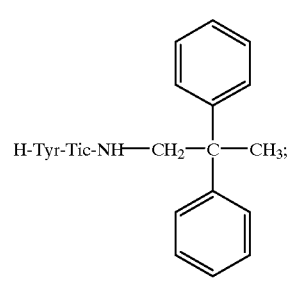
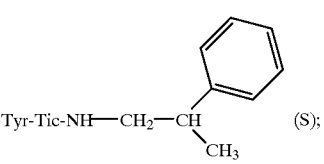
(S);
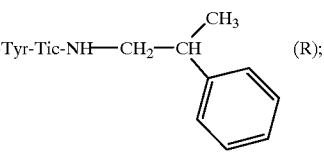
(R);
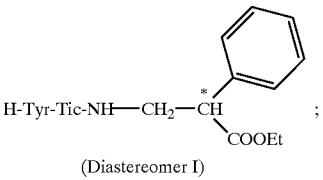
(Diastereomer I)
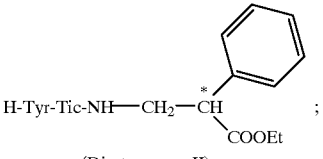
(Diastereomer II)
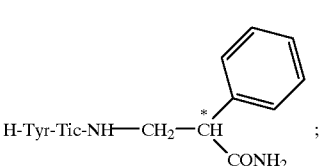
(Diastereomer I)

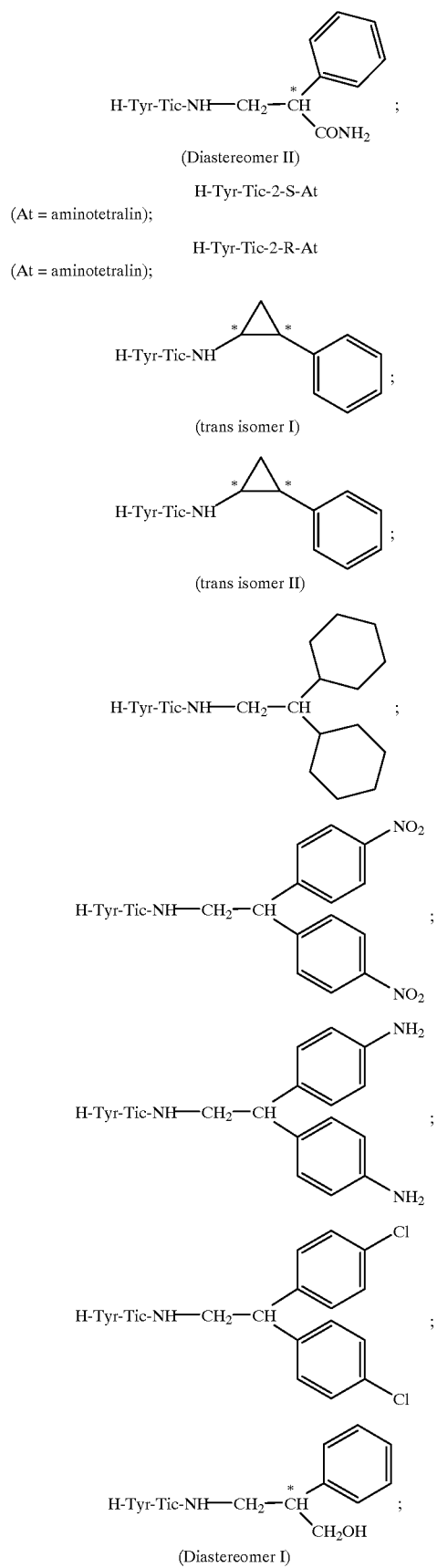
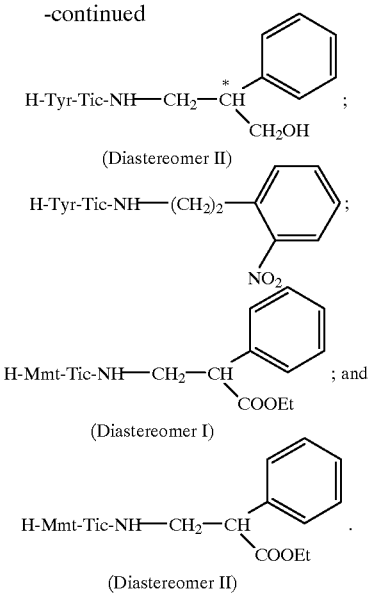
4. A method of treating a patient for pain, comprising administering to said patient an effective amount of a compound selected from the group consisting of:
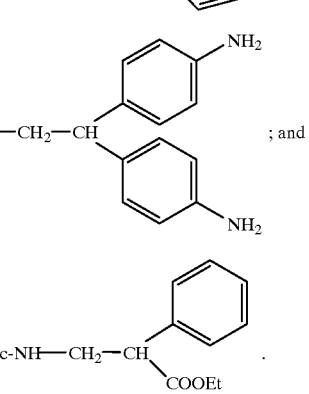
* * * * *